(12) United States Patent  
Kawate

(10) Patent No.: US 7,102,753 B2  
(45) Date of Patent: Sep. 5, 2006

(54) OPTICAL SYSTEM FOR MEASUREMENT

(75) Inventor: Etsuo Kawate, Ibaraki (JP)

(73) Assignee: National Institute of Advanced Industrial Science and Technology, Ibaraki (JP)

( * ) Notice: Subject to any disclaimer, the term of this patent is extended or adjusted under 35 U.S.C. 154(b) by 199 days.

(21) Appl. No.: 10/785,055

(22) Filed: Feb. 25, 2004

(65) Prior Publication Data

US 2004/0169863 A1 Sep. 2, 2004

(30) Foreign Application Priority Data

Feb. 27, 2003 (JP) ............................. 2003-051084

(51) Int. Cl.  
    *G01N 21/55* (2006.01)
(52) U.S. Cl. ..................................... 356/445
(58) Field of Classification Search .................. None  
    See application file for complete search history.

(56) References Cited

U.S. PATENT DOCUMENTS

| | | | | |
|---|---|---|---|---|
| 5,048,970 A | * | 9/1991 | Milosevic et al. | 356/445 |
| 5,509,733 A | * | 4/1996 | Danley | 374/11 |
| 6,033,470 A | * | 3/2000 | Fujii et al. | 117/44 |
| 6,128,093 A | * | 10/2000 | Niikura | 356/432 |
| 6,914,680 B1 | * | 7/2005 | Kawate | 356/434 |
| 2004/0008346 A1 | | 1/2004 | Kawate | |

FOREIGN PATENT DOCUMENTS

| | | | |
|---|---|---|---|
| JP | 62-132152 A1 | 6/1987 | |
| JP | 64-035306 A1 | 2/1989 | |
| JP | 5-133880 | * | 5/1993 |
| JP | 11-183320 A | 7/1999 | |
| JP | 2000-180351 A | 6/2000 | |
| JP | 2002-296111 A | 10/2002 | |
| JP | 2002-296111 A1 | 10/2002 | |

OTHER PUBLICATIONS

L. Ward, et al. "A theoretical study of the sensitivities of somne normal incidence methods for measuring the optical constants and thicknesses of thin films" Brit. J. Appl. Phys., vol. 18, pp. 277-284, (1967).  
J. E. Nestell, Jr., et al. "Derivation of Optical Constants of Metals from Thin-Film Measurements at Oblique Incidence", Applied Optics, vol. 11, No. 3, pp. 643-651, (Mar. 1972).  
Leonard Hanssen et al. "Methods for absolute reflectance measurement of transmissive materials in the infrared" SPIE, vol. 3425, pp. 16-27, (Jul. 1998).  
Etsuo Kawate "Symmetry X system and method for absolute measurements of reflectance and transmittance of specular samples" Applied Optics, vol. 42, No. 25, pp. 5064-5072 (Sep. 2003).  
Japanese Office Action dated Dec. 12, 2004.

\* cited by examiner

*Primary Examiner*—Michael P. Stafira  
(74) *Attorney, Agent, or Firm*—Rader, Fishman & Grauer, PLLC

(57) ABSTRACT

In an optical system, first and second optical paths intersected with each other on a sample holder are set, wherein the first and second optical paths are formed so that light from a light source is projected to be converged on the intersection from an incoming side beam switching mirror that selectively switches a direction of the light via one of first and second converged light reflectors, first and second received light reflectors that projects the light to an exiting side beam switching mirror disposed on the first and second optical paths respectively, the exiting side beam switching mirror switches a direction of the light projected from one of the first and second received light reflectors, and intensity of light from the sample in case of face side incidence and back side incidence to the sample can be measured.

4 Claims, 7 Drawing Sheets

PRIOR ART

OPTICAL SYSTEM FOR MEASUREMENT

TECHNICAL FIELD OF THE INVENTION

The present invention relates to an optical system capable of measuring, at an arbitrary angle, intensity of outgoing light such as regularly reflected light, transmitted light, scattered light, or light emission from a sample, when light is incident to the sample at an arbitrary incident angle.

DESCRIPTION OF RELATED ART

Optical technology is utilized in high speed large capacity optical communication, image processing, etc. in the IT industry, a laser knife, cancer treatment, etc. in the medical industry, the nano-technology, isotope separation, a display, an illumination appliance, etc. using laser beam in the manufacturing/processing industry, and precise optical measurement, information processing technology development, etc. in the academic field, and is a very important technology in modem life.

In the basic technology for supporting this optical technology, determination of the optical constants (refractive index and attenuation coefficient) of substance, in other words, the complex dielectric constant is important. In order to determine these two unknowns (the refractive index and the attenuation coefficient), it is necessary to carry out two independent measurements.

In one of the methods, in case of a transparent sample such as dielectric, the optical constant is determined by measuring the absolute reflectance and the absolute transmittance of the transparent sample at one predetermined angle, and solving the simultaneous equations thereof.

For example, see Japanese Laid Open Patent No. 64-35306.

In case of a non-transparent sample such as metal, the optical constant of the sample is determined by measuring the absolute reflectance at two different incident angles, and solving the simultaneous equations thereof. These methods are intuitive, and versatile.

See Japanese Laid Open Patent No. 62-132152.

The reflectance and the transmittance of a sample are measured by different optical systems respectively in a conventional dispersion type spectrophotometer for visible and ultraviolet ray range, and a conventional Fourier transformation type spectrophotometer for infrared ray range. Thus, in order to measure two quantities (reflectance and transmittance), troublesome "replacement" of part of the optical system is necessary at least during the measurement. In addition, this "replacement" is a considerable error factor to the result of measurement.

In addition, more specifically, the absolute transmittance is determined as the ratio of the light intensity according to presence and absence of a sample on an incoming optical axis of the incoming light. In this case, since the sample and a detector may be arranged in a row on the optical axis of the incoming light, the measurement is easy. On the other hand, the measurement of the absolute reflectance is determined as the ratio of the light intensity according to the presence and absence of the sample. In this case, if the sample is absent, the light passes in the direction of the incoming light. On the other hand, if the sample is present, the passing direction of the reflected light is different from the original direction of the incoming light due to the reflection. As a result, it is difficult to measure the reflectance.

For the measurement of this absolute reflectance, a method (goniometric method) for moving the detector, and a method (V-N method and V-W method) for moving an additional mirror while the detector is fixed have been developed. As to the goniometric method, see Japanese Patent No. 64-35306. As to the V-N method, see Japanese Laid Open Patent No. 62-132152. As to the V-W method, for example, see Japanese Laid Open Patent No. 62-132152. All the methods described above are disclosed in "Proceeding of SPIE, vol. 3425 (1998), PP16–27."

FIGS. 7A and 7B describe a method for measuring the absolute reflectance by a conventional goniometric method. In this goniometric method, exiting light from a light source LS of a spectrophotometer, etc. is converged at a sample holder SH, and the transmitted or reflected light is detected by a detector D. The sample holder SH has a through hole B and a sample T, and slides to select either of them.

In the measurement, as shown in FIG. 7A, the through hole B is selected by the sample holder SH, and a background signal is measured by the detector D. The incident angle in this state is defined as $\theta$. Next, the sample holder SH is allowed to slide so as to select the sample T, the detector D is rotated by $(180°-2\theta)$ with respect to the center of the sample, and a sample signal reflected by the sample is measured (refer to FIG. 7B). By calculating the ratio of the sample signal to the background signal, the absolute reflectance at the incident angle $\theta$ can be determined.

In this goniometric method, the absolute transmittance can also be measured. In this case, as shown in FIG. 7A, the through hole B held in the sample holder SH is selected, and a background signal is measured by the detector D as in the case of measurement of the absolute reflectance. Next, the sample holder SH is allowed to slide so as to select the sample T, and the detector D can measure the sample signal transmitted through the sample T approximately at the same place. The absolute transmittance at the incident angle $\theta$ is determined as the ratio of these two quantities.

Also see British Journal Applied Physics, vol. 18, PP227–284 (1967) (BRIT. J. APPL. PHYS. Vol. 18 (1967)), and Applied Optics, Vol. 11, PP643–651 (1972) (APPL. OPTICS vol. 11 (1972)).

In the conventional measurement of the absolute reflectance, the detector or the mirror must be moved. Reproducibility of the movement of this detector or the mirror considerably influences the measurement errors. As described above, in the conventional measurement of the absolute reflectance, in general the measurement accuracy is poor, and the accuracy is about several % in the measurement of the absolute reflectance using a spectrophotometer in the market.

In addition, in the goniometric method, the absolute reflectance can be measured at an arbitrary incident angle while the incident angle cannot be generally changed in other V-W method or V-N method.

Regarding the measurement of the light scattering from the sample, there have conventionally been two methods. In one of the two methods, the detector is moved at the angle other than that of the regular reflection from the sample in the goniometric method. In the other methods, that is, a method using the integrating sphere, the sample is set in an integrating sphere and the regularly reflected light is allowed to escape outside the integrating sphere so as to measure the scattered light. In this method using the integrating sphere, only the mean light scattering is determined. The angle dependency of the light scattering by the sample can be determined by the above goniometric method in principle, but the measurement is very difficult.

Further, in case of a film sample on a substrate, fringe appears in a reflection or transmittance spectrum since in general multiple reflections take place in the substrate. The fringe deteriorates the accuracy of measurement when the optical characteristic of the film is measured with high accuracy. Although in order to measure the spectrum without fringe to prevent the multiple reflections from taking place in the substrate, it is possible to accomplish this by allowing light of P-polarization to enter to the sample at the Brewstar angle to the substrate. Since the Brewstar angle is a function of wavelength, the wavelength must be changed every time the wavelength is changed. Although this measurement can be accomplished by the goniometric method in principle, it is impossible in fact to move the goniometer with high reproducibility every time.

SUMMARY OF THE INVENTION

An object of the present invention is to solve these conventional problems, and more specifically, to provide an optical system capable of simultaneously measuring the reflectance and transmittance of a sample at an arbitrary angle without using any different optical systems for measuring the reflectance and the transmittance of the sample, and without necessity to "replace" part of the optical system during the measurement thereby eliminating factors for large errors of the measurement result Another object of the present invention is to provide an optical system for simultaneously measuring reflectance and transmittance of a sample at an arbitrary angle, which is capable of easily built in a dispersion type spectrophotometer extensively used in the wavelength range shorter than that of near infrared rays, or a Fourier transformation type spectrophotometer used in the wavelength range longer than that of near infrared rays.

It is still another object of the present invention to provide an optical system for easily, and accurately, and simultaneously measuring reflectance and transmittance of a sample even in not only the a dispersion type spectrophotometer and a Fourier transformation type spectrophotometer but also the system comprising an external light source such as X-ray light source, synchrotron radiation light source, a laser beam or microwave light source, and an appropriate detector.

Still another object of the present invention is to provide an optical system for measuring reflectance and transmittance for the face side incidence and the back side incidence by allowing light to be incident on a sample from the face side and the back side, respectively.

Still another object of the present invention is to provide an optical system for measuring reflectance and transmittance at an arbitrary incident angle, and measuring the spectrum not influenced by multiple reflections within a substrate in a composite sample such as a thin film on the substrate.

Still another object of the present invention is to provide an optical system capable of measuring light scattering or light emission by a sample.

In view of the above problems, the present invention provides an optical system for measurement, wherein first and second optical paths intersected with each other at an intersection on a sample holder are set, wherein the first and second optical paths are formed so that light from a light source is projected so as to be converged on the intersection from an incoming side beam switching mirror for selectively switching a direction of the light via one of first and second converged light reflectors, wherein first and second received light reflectors for projecting the light to an exiting side beam switching mirror are disposed on the first and second optical paths respectively, and the exiting side beam switching mirror is capable of switching a direction of the light projected from one of the first and second received light reflectors so that the light is projected toward a detector, and wherein intensity of light from the sample in case of face side incidence and back side incidence to the sample can be measured therein.

The optical-system for measurement, the first and second converged light reflectors and the first and second received light reflectors may be elliptic cylindrical mirrors having an opening portion respectively, and each of the elliptic cylindrical mirrors can be disposed so that center axes of the elliptic cylindrical mirrors are parallel to each other. Each focal axis of the elliptic cylindrical mirrors is located on a common focal axis.

In the present invention, a line of focal points formed by a bi-elliptic cylindrical mirror is defined and hereinafter referred to as "a focal axis".

The elliptic cylindrical mirrors are coupled with each other at the respective opening portions, wherein the sample holder is placed on the common focal axis, and the incoming side beam switching mirror and the exiting side beam switching mirror is disposed on remaining two focal axes respectively, and an incoming through hole and an exiting through hole are disposed on an incoming side and an exiting side of the elliptic cylindrical mirrors respectively.

In the optical system for measurement, the sample holder may selectively position a sample and a reference sample at the intersection of the first and second optical paths, and the incoming side beam switching mirror and the exiting side beam switching mirror may be rotatable with mutual relation, whereby reflectance and transmittance can be measured simultaneously at arbitrary incident angle.

In the optical system for measurement, the reference sample may be a through hole whereby absolute reflectance and absolute transmittance can be measured simultaneously at an arbitrary incident angle.

In the optical system for measurement, the exiting side beam switching mirror may be independently rotatable whereby light scattering and light emission of the sample by the light from the light source can be measured.

In a case of a composite sample such as the thin film sample on the substrate, an incident angle on the sample may be selected to be the Brewster's angle with respect to the substrate by appropriately selecting a setting angle of an incoming side beam switching mirror, and appropriately selecting a setting angle of an exiting side beam switching mirror, with the incoming light on the sample being the P polarized light, whereby the optical measurement of the thin film which is not influenced by the multiple reflection within the substrate can be accomplished.

Further, the optical system according to the present invention may be capable of being built in a dispersion type spectrophotometer or Fourier transformation type spectrophotometer.

The present invention will become more apparent from the following detailed description of the embodiments and examples of the present invention.

DETAILED DESCRIPTION OF THE INVENTION

Embodiments of a bi-elliptic cylindrical mirror in accordance with the present invention will be described in detail with reference to FIGS. 1 through 5.

Figure 1:
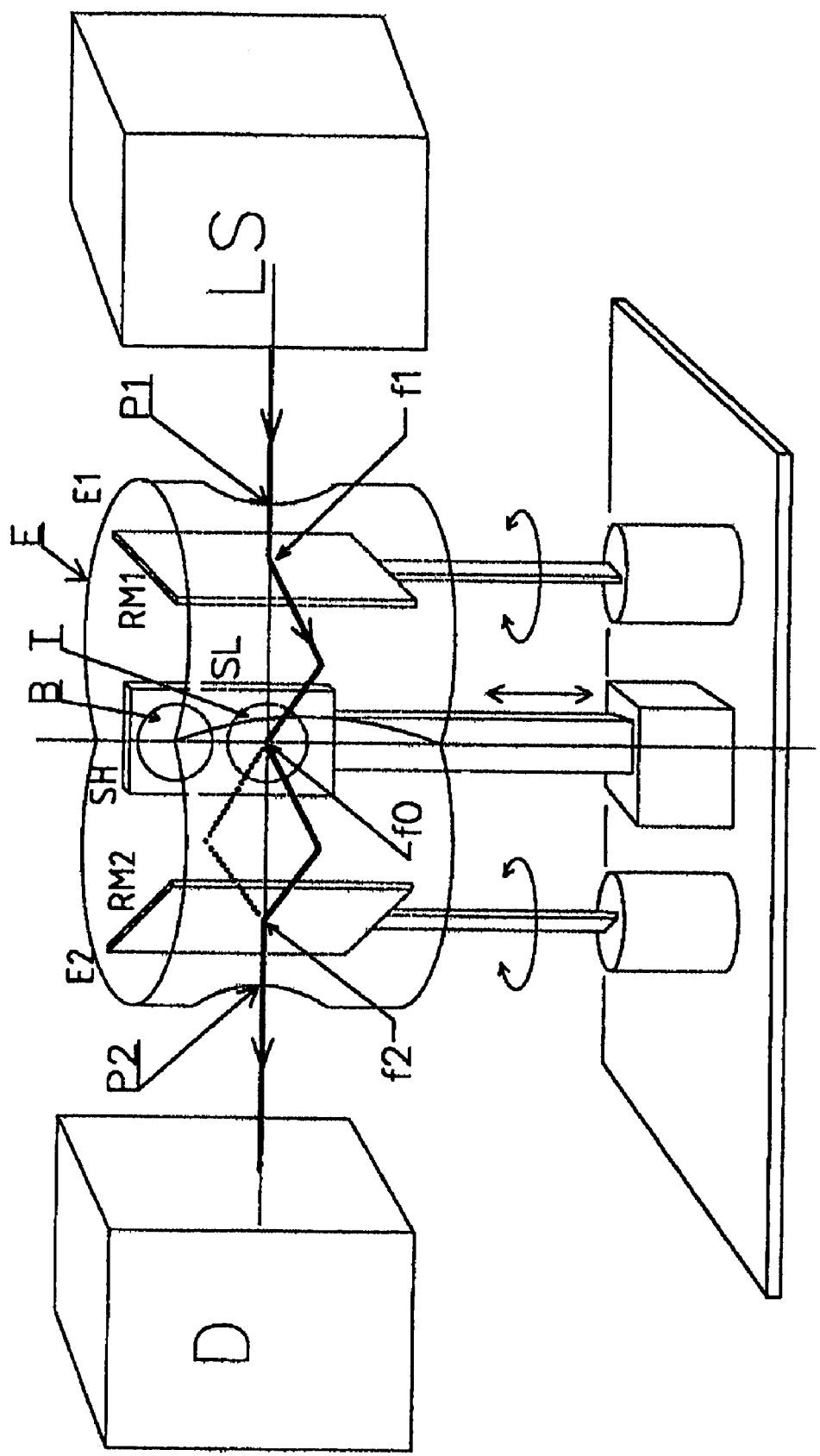
FIG. 1 is a perspective view of an optical system according to the present invention, showing inside thereof.

In this embodiment, a bi-elliptic cylindrical mirror E comprising a first elliptic cylindrical mirror E1 and a second elliptic cylindrical mirror E2 shown in FIG. 1 is used as converged light reflectors and received light reflectros. Thus, an optical system of the embodiment comprises the bi-elliptic cylindrical mirror E is equipped with the two elliptic cylindrical mirrors E1 and E2, an incoming side beam switching mirror RM1 and an exiting side beam switching mirror RM2, and a sample holder SH.

In the bi-elliptic cylindrical mirror E, the two elliptic cylindrical mirrors E1 and E2 are disposed adjacent to each other so that the respective center axes are parallel to each other.

Each of the elliptic cylindrical mirrors is cut in a plane which is perpendicular to a line connecting two focal axes of the mirrors and includes two focal axes of each mirror adjacent to each other.

These two elliptic cylindrical mirrors E1 and E2 are integrally coupled with each other at the respective opening portions so that the respective cut sides of the elliptic cylindrical mirrors are agreed with each other, and each focal axis of the elliptic cylindrical mirrors E1 and E2 is located on a common focal axis f0.

In addition, an incoming side through hole P1 and an exiting side through hole P2 are formed in an incoming side of the first elliptic cylindrical mirror E1, and in an exiting side of the second elliptic cylindrical mirror E2, respectively.

In manufacturing the bi-elliptic cylindrical mirror E as shown in FIG. 1, two elliptic cylindrical mirrors E1 and E2 of a suitable length with insides thereof being mirror finished are prepared. Each of the prepared two elliptic cylindrical mirrors are cut off along the plane perpendicular to a line connecting two focal axes of elliptical cylindrical mirrors, and having one of the focal axes of the elliptical cylindrical mirror.

The two elliptic cylindrical mirrors E1 and E2 are connected so that each focal axes included in each cut-off plane is located on common focal axis f0 respectively and the common focal axis f0 and two remaining focal axes f1 and f2 are arranged on one line.

Hereinafter, the line passing through these three focal axes at half point of the height of elliptic cylinder is called an optical axis.

Two through holes as the incoming side through hole P1 and the exiting side through hole P2 are formed along the optical axis at the intersecting points of the optical axis and both sides of the elliptic cylindrical mirrors E1 and E2.

An external light source LS which emits light to the incoming side through hole P1 is disposed on the optical axis, and a detector D for detecting light exiting from the exiting side through hole P2 is disposed on the optical axis. In addition, the sample holder SH is disposed on the common focal axis f0, and the incoming side beam switching mirror RMI and the exiting side beam switching mirror RM2 are disposed on the two remaining focal axes f1 and f2 of the elliptic cylindrical mirror, respectively. The direction of these beam switching mirrors can be controlled whereby an optical arrangement for allowing the incidence at an arbitrary incident angle θ to the sample and for detecting exiting light coming from the sample at an arbitrary exiting angle can be obtained.

Two holes of the same size are formed in a slide member SL so that the sample T or a reference sample B can be attached thereto whereby it is possible to switch therebetween. The beam switching mirrors RM1 and RM2 can also be operated so as to work with the slide member in an interlocking manner by an interlocking mechanism (not shown) when switching this slide member. As a result, the detector D or mirrors need not be moved, and the conventionally required "replacement" becomes unnecessary, thereby improving the reproducibility of data of the absolute reflectance and the absolute transmittance, and reducing measurement errors.

Next, the operation of the embodiment will be described.

In FIG. 1, light emitted from the light source LS such as the external light source or a spectrophotometer goes along with the optical axis of the bi-elliptic cylindrical mirror E, and passes through the incoming side through hole P1 so as to enter the inside of the elliptic cylindrical mirror E1. This incoming light reaches the incoming side beam switching mirror RM1, and the light is reflected by this beam switching mirror RM1. The reflected light reaches the elliptic cylindrical mirror E1 and is reflected thereby, and converged on the sample T on the common focal axis f0.

A surface of the sample on the sample holder SH is set parallel to the common focal axis of the bi-elliptic cylindrical mirror E. The light from this sample (reflected light or transmitted light) reaches and is reflected on the elliptic cylindrical mirror E2, and is converged on the exiting side beam switching mirror RM2. The light reflected by the exiting side beam switching mirror RM2 goes on the optical axis of the light source LS, and then reaches the detector D.

This optical system is capable of emitting incident light to the sample at an arbitrary angle and of measuring exiting light (reflected light or transmitted light) from the sample at an arbitrary angle. In this embodiment, specifically as examples, the measurement of absolute reflectance and absolute transmittance at an arbitrary incident angle will be described below with reference to FIGS. 2 to 5.

First, the reflectance determined by a combination of a proximal side surface of the elliptic cylindrical mirror E1 and the elliptic cylindrical mirror E2 is defined as r, and the reflectance determined by a combination of a distal side surface of the elliptic cylindrical mirror E1 and the elliptic cylindrical mirror E2 is defined as r'.

In addition, the angle at which the incoming side beam switching mirror RM1 is directed in the direction of the light source LS and perpendicular to the optical axis of the bi-elliptic cylindrical mirror E is defined to be zero degree. On the other hand, the angle at which the exiting side beam switching mirror RM2 is directed in the direction of the detector D and perpendicular to the optical axis of the bi-elliptic cylindrical mirror E is defined to be zero degree.

Absolute reflectance measured from a surface of the sample will be described.

Figure 2:
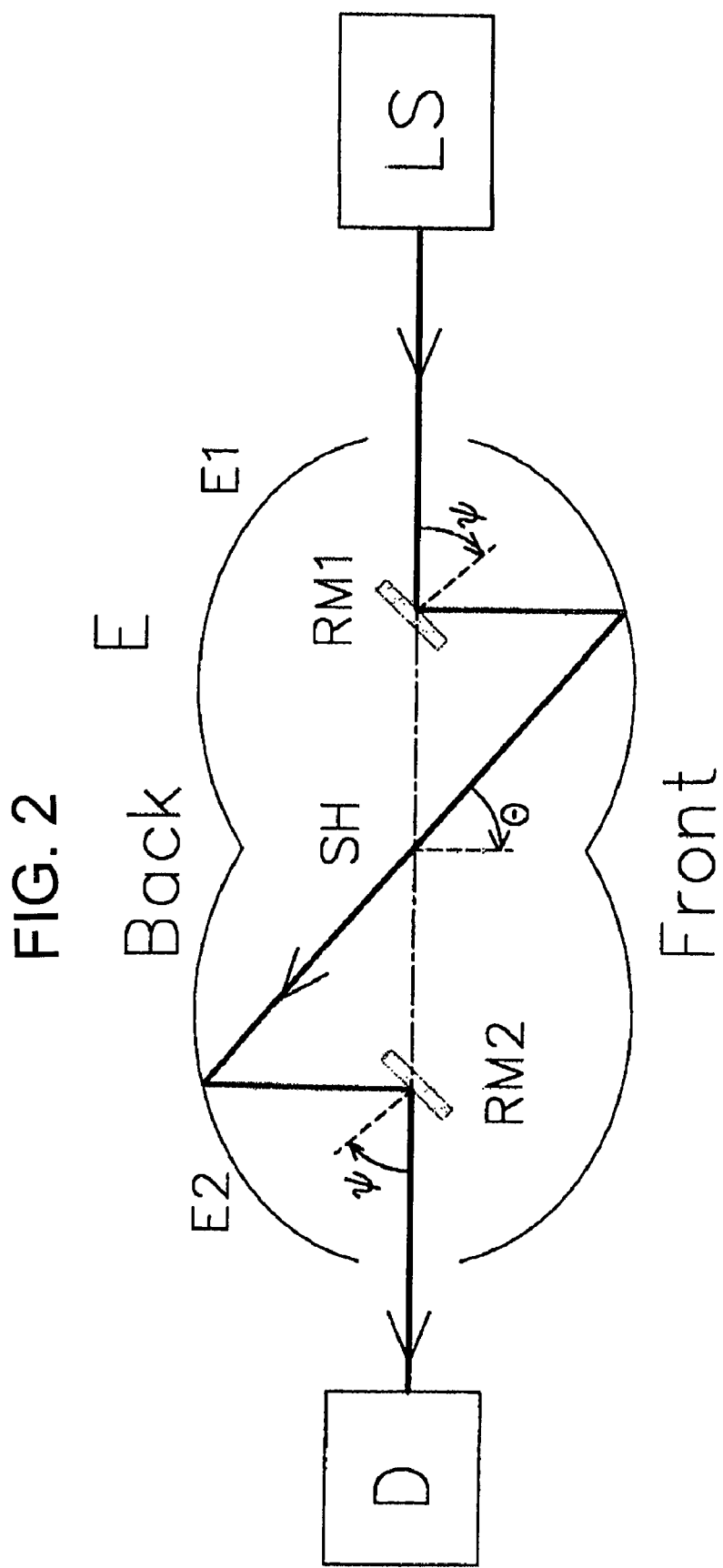
FIG. 2 is a schematic view illustrating the measurement of background for face side incidence according to the present invention.
Figure 3:
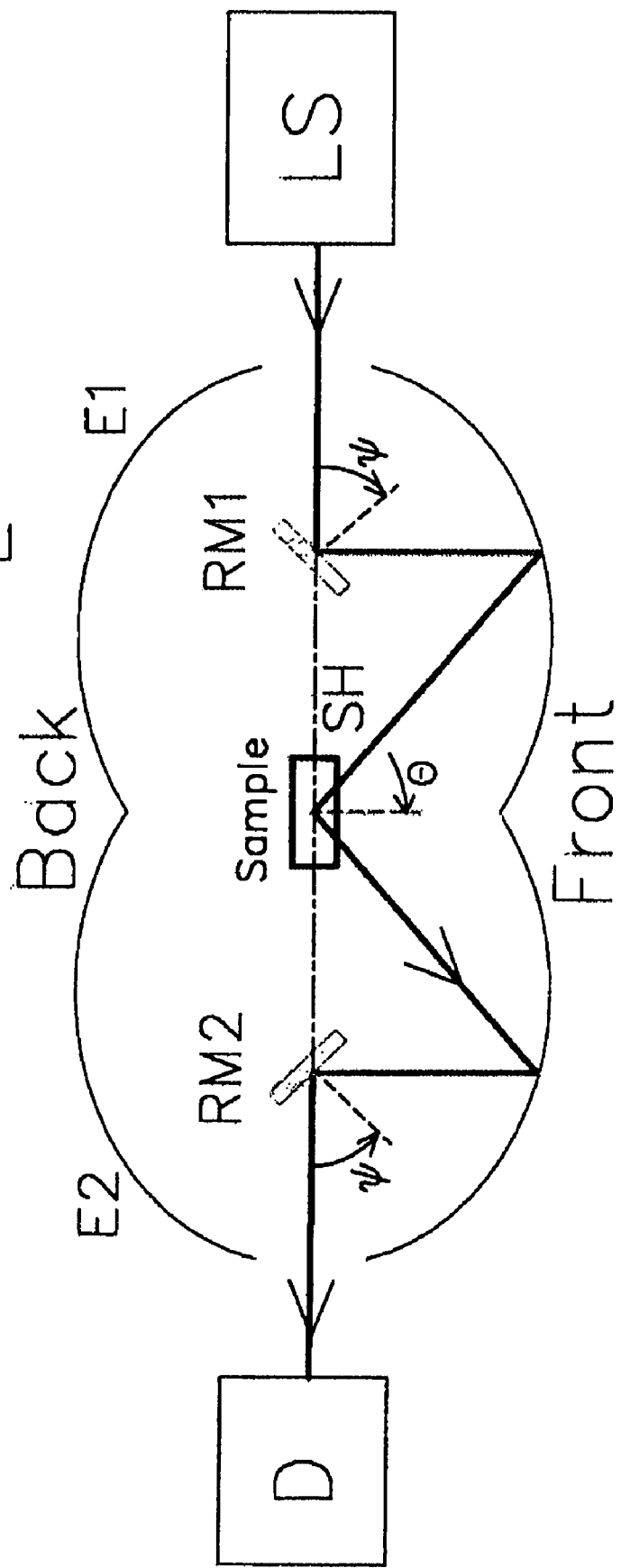
FIG. 3 is a schematic view illustrating the measurement of sample reflection for face side incidence according to the present invention.

In FIGS. 2 and 3, light emitted from the light source LS goes on the optical axis of the bi-elliptic cylindrical mirror E. In this case, the angle at which the incoming light reflected by the incoming side beam switching mirror RM1 by appropriately rotating the incoming side beam switching mirror RM1 clockwise is projected on an inner surface of the proximal side of the elliptic cylindrical mirror E1 in FIG. 2 (hereinafter, referred to as "a front surface") is defined as ψ (degrees). In this state, the light reflected by the elliptic cylindrical mirror E1 is incident from the face side of the sample holder SH at the incident angle of θ degrees.

In order to measure a background signal, the through hole B of the sample holder SH at which no reference sample is attached is selected, and the incoming light passes through the through hole B provided in the sample holder SH as shown in FIG. 2, and is reflected by an inner surface on the distal side of the elliptic cylindrical mirror E2 in FIG. 2 (hereinafter, referred to as "a back surface"), and converged on the exiting side beam switching mirror RM2.

In this state, by rotating the existing beam switching mirror RM2 by ψ degrees clockwise, the light reflected by the exiting side beam switching mirror RM2 goes on the original optical axis. Thus, the light is converged on the detector D. The output in this state is defined as Io.

Next, in order to measure the sample signal of the sample, if the sample T attached to the sample holder SH is selected, as shown in FIG. 3, the incoming light is reflected by the sample, reflected by the front surface of the elliptic cylindrical mirror E2, and converged on the exiting side beam switching mirror RM2. By rotating the exiting side beam switching mirror RM2 counterclockwise by approximately ψ degrees, the light reflected by the exiting side beam switching mirror RM2 goes on the same optical axis. Thus, the light is converged on the detector D. In this state, the output is defined as Ir. The reflectance r from the face side of the sample is determined as r=Ir/Io.

Figure 4:
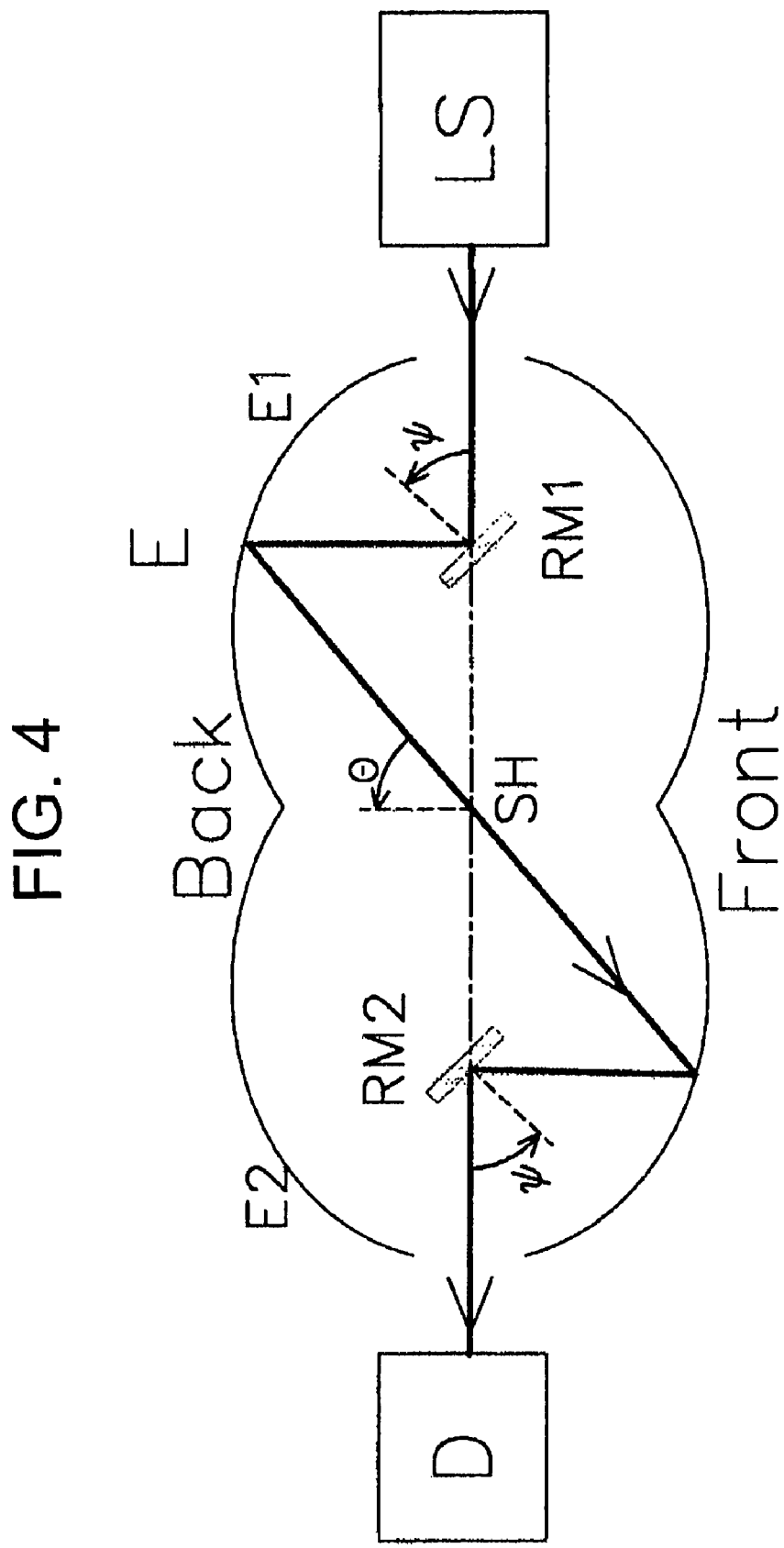
FIG. 4 is a schematic view illustrating the measurement of background for back side incidence according to the present invention.
Figure 5:
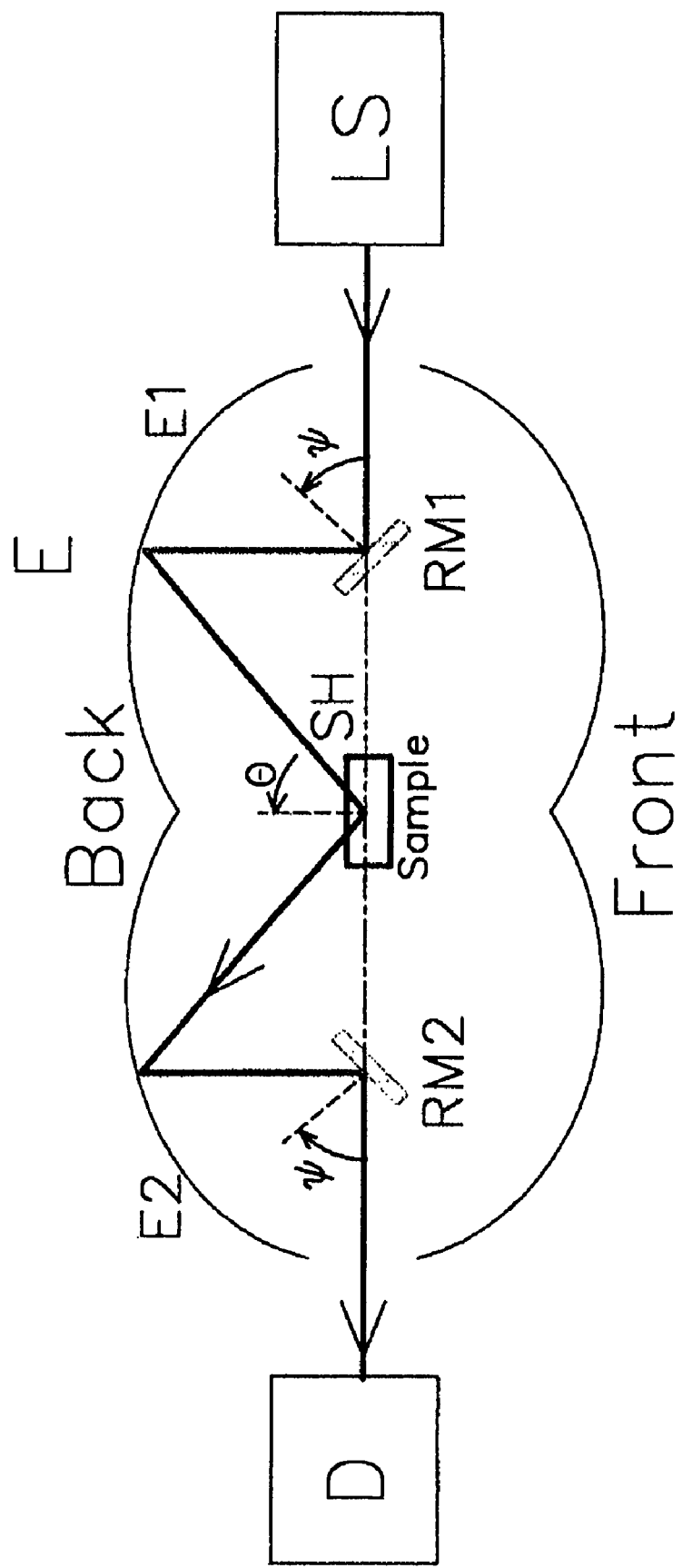
FIG. 5 is a schematic view illustrating the measurement of sample reflection for back side incidence in the present invention.

In measurement of reflectance from the back side of the sample, in FIGS. 4 and 5, the angle at which the light from the light source LS is received by the incoming side beam switching mirror RM1 which is turned counterclockwise, and the incoming light reflected by the incoming side beam switching mirror RM1 is projected on the back surface of the elliptic cylindrical mirror E1 is defined as ψ degrees. In this state, the light reflected by the elliptic cylindrical mirror E1 is incident from the back side surface of the sample holder SH at the angle of incidence θ.

When, in order to measure a background signal, the through hole B of the sample holder SH is selected, light passes through the through hole of the sample holder SH as shown in FIG. 4, and is reflected on the front surface of the elliptic cylindrical mirror E2, and converged on the exiting side beam switching mirror RM2. In this state, the light reflected by the exiting side beam switching mirror RM2 goes on the same optical axis by rotating the exiting side beam switching mirror RM2 counterclockwise by ψ degrees. Thus, the light is converged on the detector D. The output in this state is defined as I'o.

Next, when, in order to measure a sample signal of the sample, the sample T of the sample holder SH is selected, the incoming light is reflected on the sample T as shown in FIG. 5, reflected by the back surface of the elliptic cylindrical mirror E2, and converged on the exiting side beam switching mirror RM2. In this state, the light reflected by the exiting side beam switching mirror RM2 goes on the optical axis of the original external light source by rotating the exiting side beam switching mirror RM2 clockwise by approximately ψ degrees. Thus, the light is converged on the detector D. The output in this state is defined as I'r. The reflectance r' from the back side of the sample is determined as r'=I'r/I'o.

In general, the reflectance from the face side is not equal to the reflectance from the back side (r # r').

Next, description will be given on the measurement of the absolute transmittance from the face side and the absolute transmittance from the back side of a transparent sample by using this optical system.

First, in measuring the absolute transmittance from the face side of the sample by combination of the front surface of the elliptic cylindrical mirror E1 and the back surface of the elliptic cylindrical mirror E2, in FIG. 2, the light from the light source LS is received by the incoming side beam switching mirror RM1, and the incoming light reflected on the incoming side beam switching mirror RM1 is projected on the front surface of the elliptic cylindrical mirror E1 by appropriately rotating the incoming side beam switching mirror RM1 clockwise, and the angle in this state is defined as ψ degrees. The light reflected by the elliptic cylindrical surface E1 is incident from the face side of the sample holder SH at the incident angle θ.

In order to measure a background signal, when the through hole B of the sample holder SH is selected, the light passes through the through hole B of the sample holder SH as shown in FIG. 2, and is reflected by the back surface of the elliptic cylindrical mirror E2, and converged by the beam switching mirror RM2. In this state, the light reflected on the exiting side beam switching mirror RM2 goes on the original optical axis of the light source LS by turning the exiting side beam switching mirror RM2 clockwise by ψ degrees. Thus, the light is converged on the detector D. The output in this state is defined as Io.

Next, in order to measure the sample signal of the sample, when the sample T attached to the sample holder SH is selected, in FIG. 2, the light transmitted through the sample T out of the incoming light is reflected by the back surface of the elliptic cylindrical mirror E2, and converged on the exiting side beam switching mirror RM2. In this state, the light reflected on the exiting side beam switching mirror RM2 goes on the original optical axis by turning the existing side beam switching mirror RM2 clockwise by approximately ψ degrees. The light is converged on the detector D thereby. When the output in this state is defined as $I_t$, the absolute transmittance t from the face side is determined as $t = I_t/Io$.

In measuring the absolute transmittance from the back side of the sample by a combination of the back surface of the elliptic cylindrical mirror E1 and the front surface of the elliptic cylindrical mirror E2, the light emitted from the light source LS is received by the incoming side beam switching mirror RM1 that is turned counterclockwise as shown in FIG. 4, and the incoming light reflected by the incoming side beam switching mirror RM1 is projected on the back surface of the elliptic cylindrical mirror E1. The angle of the incoming side beam switching mirror RM1 in this state is defined as ψ degrees, and the light reflected by the elliptic cylindrical mirror E1 is allowed to be incident from the back side of the sample holder SH at the incident angle θ.

When, in order to measure the background signal, the through hole B of the sample holder SH is selected, the light passes through the through hole B formed in the sample holder SH, and is reflected by the front surface of the elliptic cylindrical mirror E2, and converged on the exiting side beam switching mirror RM2. In this state, the light reflected on the exiting side beam switching mirror RM2 goes on the original optical axis by rotating the exiting side beam switching mirror RM2 counterclockwise by $\psi$ degrees. Thus, the light is converged on the detector D. The output in this state is defined as I'o.

When in order to measure a sample signal of the sample, the sample T of the sample holder SH is selected, in FIG. 4, the light transmitted through the sample out of the incoming light is reflected by the front surface of the elliptic cylindrical mirror E2, and converged on the exiting side beam switching mirror RM2. In this state, the light reflected on the exiting side beam switching mirror RM2 goes on the same axis by rotating the exiting side beam switching mirror RM2 counterclockwise by approximately $\psi$ degrees. Thus, the light is converged on the detector D. When the output in this state is defined as I'$_t$, the absolute transmittance t' from the back side of the sample is determined as t'=I'$_t$/I'o. The absolute transmittance from the face side is equal to the absolute transmittance from the back side in an ideal sample (t=t').

In the optical system of the embodiment using this bi-elliptic cylindrical mirror E, the incident angle $\psi$ of the incoming light on the incoming side beam switching mirror RM1 can be changed in such a range that the reflected light is projected on the elliptic cylindrical mirror E1, and the incident angle $\theta$ on the sample can also be changed so that the incident angle can thus be continuously and arbitrarily changed from about 1 degree to about 89 degrees.

In the same way, the angle $\psi$ of the exiting side beam switching mirror RM2 can be changed in such a range that of the outgoing light from the sample is emitted to the elliptic cylindrical mirror E1, and the outgoing light measuring angle $\theta$ from the sample can also be changed so that the measuring angle can thus be continuously and arbitrarily changed from about 1 degree to about 89 degrees.

By using this optical system according to the embodiments of the present invention using the bi-elliptic cylindrical mirror E, in a transparent substance such as dielectric, both the absolute reflectance and the absolute transmittance are measured at a predetermined incident angle, and these simultaneous equations including two unknowns of the refractive index and the attenuation coefficient (optical constants) are solved to determine the optical constants with excellent accuracy.

In addition, by using the bi-elliptic cylindrical mirror E according to the embodiments of the present invention, the absolute reflectance can be measured at an arbitrary angle of incidence so that for non-transparent samples such as metal, the absolute reflectance is measured at two different incident angles, and simultaneous equations including two unknowns of the refractive index and the attenuation coefficient (optical constants) are solved to determine the optical constants with excellent accuracy.

Further, in this optical system according to the embodiments of the present invention, scattered light or emission of light by the sample can also be measured by fixing the incoming side beam switching mirror RM1 and changing the above angle $\psi$ of the exiting side beam switching mirror RM2.

In addition, since this optical system according to the embodiments of the present invention, is capable of continuously changing the incident angle of the sample, it is possible to measure the spectrum not affected by the multiple reflection inside a substrate in a composite sample such as a thin film on the substrate. As a result, the optical constant of the thin film can be determined with excellent accuracy.

In addition, as another measuring method using the bi-elliptic cylindrical mirror E, the thin film on a substrate as a sample attached to the sample holder SH is selected and S polarized light and P polarized light are incident on the thin film sample on the substrate while changing the incident angle, the polarized state of the reflected light is measured, and further, as an appropriate reference sample B, for example, a substrate is selected, the S polarized light and the P polarized light are allowed to be incident on the substrate while changing the angle of incidence, the polarized state of the reflected light is measured, and information on the optical constant of the thin film is determined from the difference of these two polarized states.

In addition, when a transparent substance having the refractive index larger than that of the sample is closely affixed to the sample, and held by the sample holder SH, and further the light is allowed to be incident thereto while changing the incident angle, attenuation of the light occurs due to the absorption on the sample when the angle is larger than the angle for total reflection. Next the material is held on the sample holder as a reference sample, and the light reflected thereon is measured while changing the incident angle as well. The optical information etc. with regard to the depth direction of the sample can be obtained based on the difference between these two reflectances.

Figure 6:
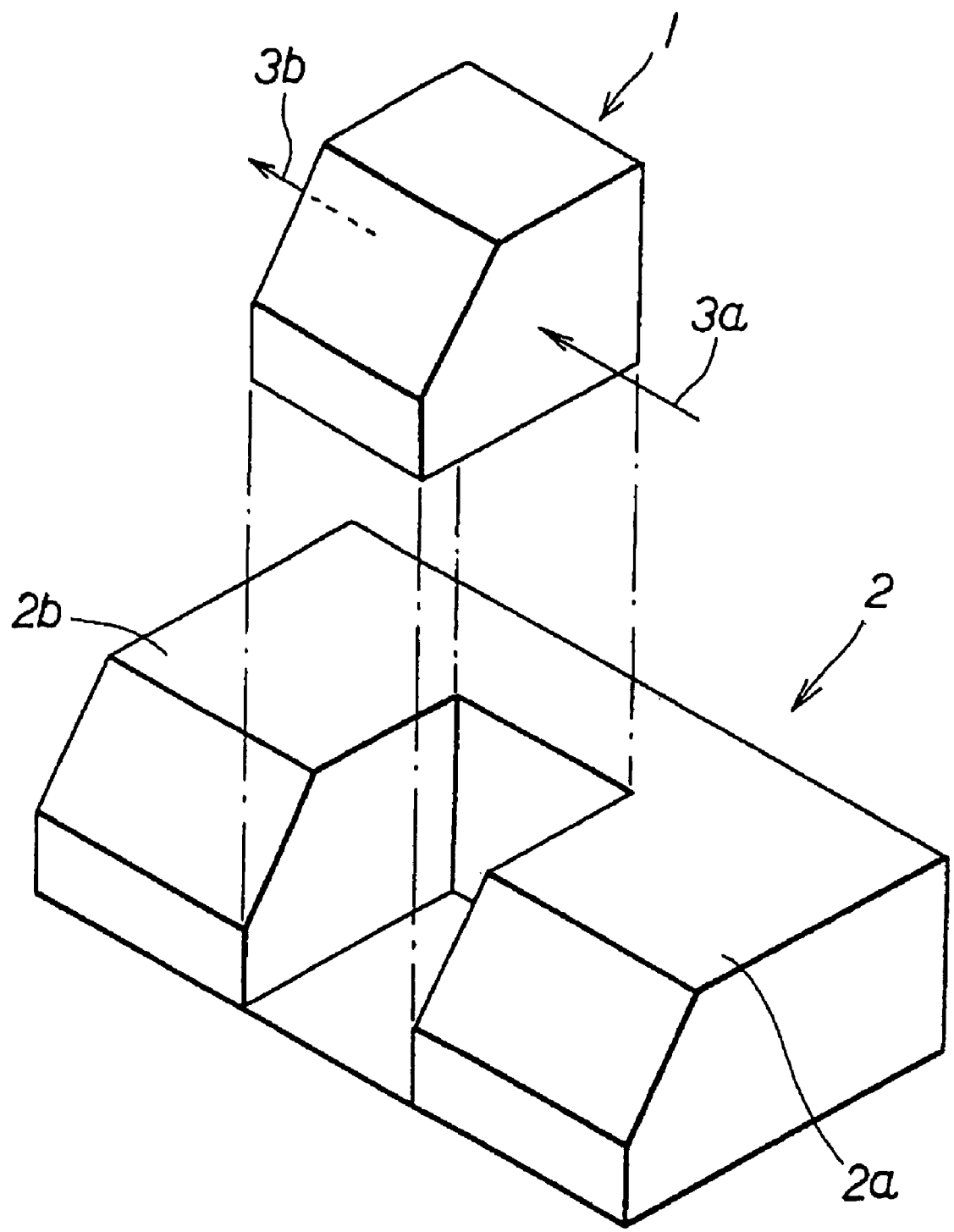
FIG. 6 is a perspective view illustrating the assembly of the optical system in a spectrophotometer according to the present invention.
Figure 7A:
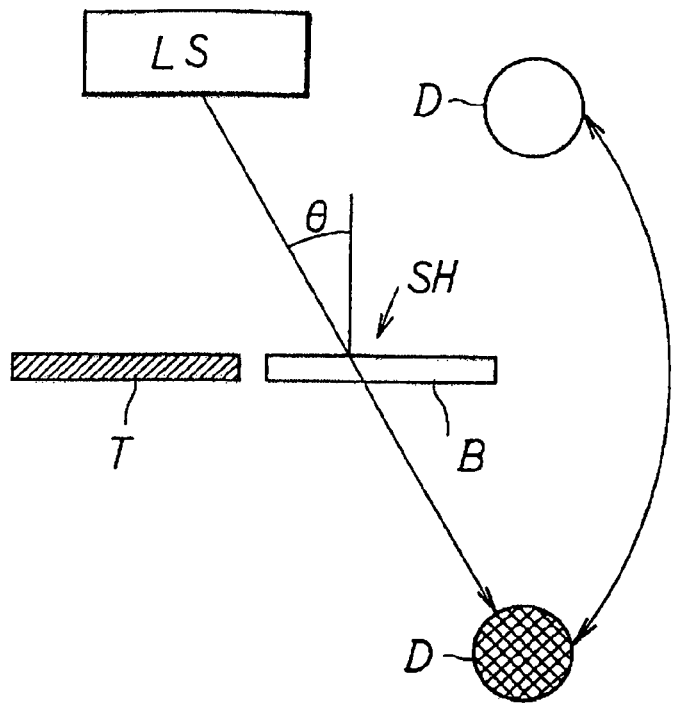
FIGS. 7A and 7B are schematic view illustrating a method for measuring the absolute reflectance by a conventional goniometric method.
Figure 7B:
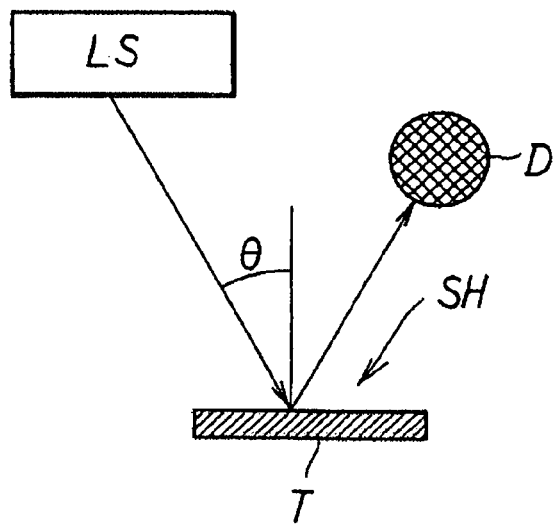

The optical system comprising the bi-elliptic cylindrical mirror capable of continuously changing an incident angle and of measuring outgoing light at an arbitrary angle can be as shown in FIG. 6 inserted in a sample chamber of a spectrophotometer which is sold in the market so that the measurement described above can be carried out.

The present invention is described with reference to the above embodiments. However, the present invention is not limited to these embodiments, and it goes without saying that the embodiments can be arbitrarily modified within the technical scope of the claims.

By the structure of the optical system using the bi-elliptic cylindrical mirror according to the present invention, it is possible to apply it to the spectrophotometer etc. sold in the market and to improve the accuracy of measurement of the spectrophotometer and further, expand function thereof. As a result, this optical system is used widely in the society and it is also expected that the present invention is useful in social, economic and academic developments.

According to the present invention of the optical system using the bi-elliptic cylindrical mirror, it is possible to measure reflectance or transmittance with high accuracy. That is, when incoming light which is incident to the incoming side beam switching mirror of the bi-elliptic cylindrical mirror is parallel light, its angle is constant whereby incident angle to the sample is also constant. As a result, measuring accuracy of spectrum is improved. On the other hand, when the incident light to the incoming side beam switching mirror is focused light, incident light flux is conical wherein the incident angle (the angle at cone point) is not constant, and has divergence. As a result, the incident angle to the sample has divergence, thereby reducing accuracy of measurement.

Thus, the present invention possesses a number of advantages or purposes, and there is no requirement that every claim directed to that invention be limited to encompass all of them.

The disclosure of Japanese Patent Application No. 2003-51084 filed on Feb. 27, 2003 including specification, drawings and claims is incorporated herein by reference in its entirety.

Although only some exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention.

What is claimed is:

1. An optical system for measurement,
wherein first and second optical paths intersected with each other at an intersection on a sample holder are set, wherein the first and second optical paths are formed so that light from a light source is projected so as to be converged on the intersection from an incoming side beam switching mirror that selectively switches a direction of the light, via one of first and second converged light reflectors.

wherein first and second received light reflectors that projects the light to an exiting side beam switching mirror are disposed on the first and second optical paths respectively, and the exiting side beam switching mirror is capable of switching a direction of the light projected from one of the first and second received light reflectors so that the light is projected toward a detector, wherein intensity of light from the sample in case of face side incidence and back side incidence to the sample can be measured therein, wherein the first and second converged light reflectors and first and second received light reflectors are elliptic cylindrical mirrors having an opening portion respectively, wherein each of the elliptic cylindrical mirrors can be disposed so that center axes of the elliptic cylindrical mirrors are parallel to each other, and each focal axis of the elliptic cylindrical mirrors located on a common focal axis, and the elliptic cylindrical mirrors are coupled with each other at the respective opening portions, and wherein the sample holder is placed on the common focal axis, the incoming side beam switching mirror and the exiting side beam switching mirror are disposed on remaining two focal axes respectively, and an incoming through hole and an exiting through hole are disposed on an incoming side and an exiting side of the elliptic cylindrical mirrors respectively.

2. The optical system for measurement according to claim 1, wherein the sample holder selectively positions a sample and a reference sample at the intersection of the first and second optical paths, and the incoming side beam switching mirror and the exiting side beam switching mirror are rotatable with mutual relation, whereby reflectance and transmittance can be measured at arbitrary incident angle.

3. The optical system for measurement according to claim 2, wherein the reference sample is a through hole.

4. The optical system for measurement according to claim 1, the exiting side beam switching mirror is independently rotatable.

* * * * *